United States Patent [19]
Tomioka et al.

[11] Patent Number: 5,993,037
[45] Date of Patent: Nov. 30, 1999

[54] LIGHT SOURCE DEVICE FOR ENDOSCOPES

[75] Inventors: Makoto Tomioka, Hachioji; Akira Hasegawa, Akishima; Shinya Matsumoto, Machida; Takayuki Suzuki, Hachioji, all of Japan

[73] Assignee: Olympus Optical Co., Ltd., Tokyo, Japan

[21] Appl. No.: 09/144,491

[22] Filed: Aug. 31, 1998

Related U.S. Application Data

[62] Division of application No. 08/509,944, Aug. 1, 1995, Pat. No. 5,823,943.

[30] Foreign Application Priority Data

| Aug. 2, 1994 | [JP] | Japan | 6-181436 |
| Oct. 6, 1994 | [JP] | Japan | 6-242684 |
| Apr. 6, 1995 | [JP] | Japan | 7-081479 |

[51] Int. Cl.⁶ ................... F21V 7/04
[52] U.S. Cl. .......... 362/583; 362/574; 362/560; 362/293
[58] Field of Search .............. 362/583, 560, 362/574, 554, 572, 293, 268

[56] References Cited

U.S. PATENT DOCUMENTS

| 4,425,599 | 1/1984 | Rieder et al. . |
| 4,729,018 | 3/1988 | Watanabe et al. . |
| 4,807,026 | 2/1989 | Nishioka et al. . |
| 4,924,856 | 5/1990 | Noguchi . |
| 4,951,133 | 8/1990 | Onoda . |
| 5,007,408 | 4/1991 | Ieoka . |
| 5,078,150 | 1/1992 | Hara et al. . |
| 5,143,435 | 9/1992 | Kikuchi . |
| 5,513,291 | 4/1996 | Buchin ..................... 385/983 |

FOREIGN PATENT DOCUMENTS

| 57-5020 | 1/1982 | Japan . |
| 60--76888 | 5/1985 | Japan . |
| 61-82731 | 4/1986 | Japan . |
| 63-281117 | 11/1988 | Japan . |
| 3-51411 | 5/1991 | Japan . |

*Primary Examiner*—Sandra O'Shea
*Assistant Examiner*—Marshall Honeyman
*Attorney, Agent, or Firm*—Pillsbury Madison & Sutro LLP

[57] ABSTRACT

A light source device for endoscopes includes a light source for emitting white light containing the components of light belonging to a visible region and wavelength bands other than the visible region; at least, a rotary color separating filter on a field sequential system; and an infrared cutoff filter for blocking light in an infrared region, of a wavelength band of the white light. When the rotary color separating filter is disposed in an optical path from the light source to a light guide, an interference filter in which an interference film is applied to a transparent base plate is placed in the optical path. This arrangement obviates the defect of burning the entrance end of the light guide or of breaking the infrared cutoff filter.

5 Claims, 12 Drawing Sheets

INCIDENT ANGLE 0°

INCIDENT ANGLE 10°

INCIDENT ANGLE 20°

INCIDENT ANGLE 30°

INCIDENT ANGLE 40°

LIGHT SOURCE DEVICE FOR ENDOSCOPES

This application is a division of application Ser. No. 08/509,944, filed Aug. 1, 1995, now U.S. Pat. No. 5,823,943 which claimed priority from, as does this application, applications filed in Japan as No. 6-181436, filed Aug. 2, 1994, No. 6-242684, filed Oct. 6, 1994 and No. 7-081479, filed Apr. 6, 1995, the contents of the four mentioned applications being incorporated hereinto by reference.

BACKGROUND OF THE INVENTION

1. Field of the Invention

This invention relates to a light source device for endoscopes which is capable of providing illumination light most suitable for rigid endoscopes, fiberscopes, and electronic scopes on color mosaic and field sequential systems.

2. Description of Related Art

In recent years, endoscopes have been widely used in which an elongated inserting section is inserted in a body cavity to thereby observe the internal organs. Various treatments are available which use a medical instrument inserted in a channel when necessary.

Endoscopes are roughly divided into two classes: rigid endoscopes or fiberscopes for visual observation, and electronic scopes using solid state image sensors, such as charge coupled devices (CCDs), as image pickups. As the image pickup systems of color pictures of the electronic scopes, available are a field sequential system for changing illumination light in sequence into R (red), G (green), and B (blue) light, which is disclosed, for example, in Japanese Patent Preliminary Publication No. Sho 61-82731, and a color mosaic system (or simultaneous system) having a filter array, in front of a solid state image sensor, in which filters transmitting R, B, and G light are arranged in a mosaic manner, which is disclosed, for example, in Japanese Patent Preliminary Publication No. Sho 60-76888.

In general, each of such rigid endoscopes, fiberscopes, or electronic scopes is connected to a light source device which is capable of providing illumination light suitable for each scope. However, rigid endoscopes, fiberscopes, or electronic scopes on the color mosaic system differ in illumination technique from electronic scopes on the field sequential system. That is, the former requires white light, whereas the latter requires light to be changed in sequence into R, G, and B light. Thus, it is necessary to provide a particular light source device according to the type of scope used. Moreover, operation varies with the light sources used. In this way, various problems have arisen as to economical and working efficiency.

To solve such problems, a light source device for endoscopes such as that disclosed in Japanese Patent Preliminary Publication No. Sho 63-281117 is known which is capable of providing illumination light, by itself, suitable for the electronic scope on the field sequential system as well as for the rigid endoscope, fiberscope, and electronic scope on the color mosaic system.

This device, however, emits light in the infrared region of the spectrum most copiously, in addition to light in the visible region which is required for observing an object, and thus has the problem of burning the fiber end of a light guide at which light from the light source concentrates.

In order to overcome this problem, for example, as set forth in Japanese Patent Preliminary Publication No. Sho 57-5020, provision has been made for mounting an infrared absorbing filter between the light source and the light guide to prevent light on the long wavelength side of the visible region from entering the light guide so that the fiber end of the light guide is not burned. Since, however, this technique uses only one infrared absorbing filter, the temperature of the base plate of the filter is raised by absorbed infrared rays when illumination is provided for a long time. Thus, the base plate of the filter itself cannot withstand a resultant thermal expansion and will cause breakage.

Infrared cutoff filters that are available include an infrared reflecting filter in which a coating consisting of a multilayered interference film applied to a transparent base plate and its coated surface possesses the properties of reflecting infrared rays and of transmitting the other rays, and an infrared absorbing filter composed of a material absorbing infrared rays. In general, the infrared absorbing filter has a spectral transmittance characteristic such as that shown in FIG. 1, and excels in the fact that most of the light belonging to the infrared region can be blocked. If, however, the infrared absorbing filter is used by itself, as mentioned above, the base plate of the filter cannot withstand thermal expansion produced by absorbed heat and may be broken. For this reason, for example, as set forth in Japanese Utility Model Preliminary Publication No. Hei 3-51411, a technique has been used that a reflecting filter is interposed between an illumination light source and an absorbing filter so that light emitted from the illumination light source is first incident on the reflecting filter, which reflects part of the light in the infrared region, and then the remainder is absorbed by the absorbing filter to block infrared light separately. According to the embodiment of this prior art publication, the spectral transmittance characteristics of the infrared reflecting filter and the infrared absorbing filter are as shown by curves A and B, respectively, in FIG. 2.

However, even with the light source device using the arrangement of the infrared cutoff filters mentioned above, illumination provided for a relatively long time causes the entrance end of the light guide to be burned, with a resulting extreme decrease in the amount of illumination light emerging from the exit end of the light guide. Furthermore, if the light source device is used for a long time, the absorbing filter will suffer deformation and breakage because of heating.

Where a xenon lamp is used as the illumination light source for example, the causes of burning occurring at the entrance end of the light guide and of breakage in the infrared absorbing filter can be explained as follows:

FIG. 3 shows the characteristic curve of the spectral energy emissivity of a common xenon lamp. According to this diagram, the xenon lamp emits, at a very high rate, light in the infrared region of the spectrum with wavelengths of 750–1100 nm. On the other hand, according to the spectral transmittance characteristic curves of the infrared cutoff filters of the conventional light source device shown in FIG. 2, the infrared reflecting filter disposed subsequent to the illumination light source transmits most of light of wavelengths 750–800 nm and light of wavelengths 800–1100 nm at a transmittance of at least 10%. After that, the amount of transmitted light increases with increasing wavelength. The infrared absorbing filter placed behind the infrared reflecting filter completely absorbs light of wavelengths more than 900 nm, but does not completely absorb light of wavelengths 700–900 nm and transmits part thereof. Consequently, of the light of wavelengths 750–1100 nm emerging from the illumination light source, light of wavelengths 750–900 nm is not completely removed by the infrared cutoff filters and concentrates at the entrance end of the light guide. In this way, the entrance end of the light guide is burned.

The infrared absorbing filter practically absorbs infrared light of wavelengths more than 700 nm which is not completely removed by the infrared reflecting filter, and radiates heat itself. Since, as is generally known, a heating element radiates infrared light itself, therefore for the infrared absorbing filter absorbing infrared light from the illumination light source generating heat becomes a new infrared radiation source (hereinafter referred to as "a secondary light source"). Part of the infrared light emitted from this secondary light source concentrates at the entrance end of the light guide and causes burning of the entrance end.

As the amount of infrared light absorbed by the infrared absorbing filter increases, the amount of generated heat increases and the amount of infrared light emitted from the secondary light source also increases. Hence, in order to prevent the entrance end of the light guide from being burned, it is required that the amount of infrared light absorbed by the infrared absorbing filter be controlled by an infrared reflecting filter disposed on the light source side of the infrared absorbing filter. In the conventional infrared reflecting filter, as shown in FIG. 2, infrared light of wavelengths 750–1100 nm, emitted at a high rate by the xenon lamp, is not sufficiently blocked. Thus, the infrared absorbing filter mainly absorbs infrared light in this wavelength range and radiates heat to form the secondary light source, which emits a sufficient amount of infrared light to burn the entrance end of the light guide. In this case, the surface temperature of the infrared absorbing filter is as high as 400–450° C., and the infrared absorbing filter suffers from a strain because of thermal expansion and yields deformation and breakage after long term use.

Some adhesives for bonding the fiber bundle of the light guide absorb ultraviolet light. In a light guide using such an adhesive, ultraviolet light emitted from the illumination light source is responsible for the burning of the entrance end of the light guide. Since conventional infrared cutoff filters transmit most light with wavelengths shorter than 400 nm or less, light in this wavelength range is absorbed at the entrance end of the light guide to radiate heat. This situation facilitates the burning of the entrance end of the light guide.

According to the conventional infrared cutoff filters, as mentioned above, of light emitted from the illumination light source, light with wavelengths shorter than 400 nm and light with wavelengths longer than 750 nm are not completely blocked. Furthermore, the removal of infrared light of wavelengths 750–1100 nm is insufficient because the infrared reflecting filter is disposed closer to the illumination light source. In this way, there are problems of burning the entrance end of the light guide and of breaking the infrared absorbing filter.

The infrared reflecting interference filter cannot transmit 100% of the light in the visible region, resulting in decrease of the amount of light in the visible region by about 10%. On the other hand, the infrared absorbing filter absorbs not only infrared light, but also visible light, and decreases the amount of visible light by about 20%. Hence, if the infrared reflecting interference filter and the infrared absorbing filter are used in combination with each other, the amount of transmitted light in the visible region will be considerably decreased.

Where the electronic scope on the field sequential system is used, a color separating filter on the field sequential system is inserted in the optical path, in addition to the infrared absorbing filter. This color separating filter separates, in sequence, R, G, and B components from white light and transmits them, and thus the brightness of the transmitted light is reduced to about ⅓ compared with the case where the color separating filter is not inserted in the optical path. The problem is thus encountered that when the electronic scope on the field sequential system is employed, brightness, as illumination light, is insufficient.

While the infrared light emitted could burn the fiber end of the light guide and thus must be blocked, visible light also is responsible for a rise in temperature at the fiber end of the light guide because it has a considerably high energy density at a light collecting section, namely the fiber end of the light guide.

Therefore, where the rigid endoscope, fiberscope, or electronic scope on the color mosaic system is used, light in the visible region is concentrated simultaneously at the fiber end of the light guide, and the energy density of light in the visible region is increased, with the result that the temperature at the fiber end of the light guide is raised. In order to prevent strictly the burning of the fiber end of the light guide, it is necessary to remove light completely, at least, in the infrared region.

Where the electronic scope on the field sequential system is used, on the other hand, white light emitted from the light source is separated to produce, in sequence, R, G, and B components, which are concentrated at the fiber end of the light guide. In this way, the energy density of light in the visible region at the fiber end of the light guide is reduced to nearly ⅓ compared with the case where the rigid endoscope, fiberscope, or electronic scope on the color mosaic system is used. Thus, the temperature at the fiber end of the light guide is not very high, and even though light in the infrared region emitted from the light source is not completely eliminated, the fiber end of the light guide will not be burned in the case where the rigid endoscope, fiberscope, or electronic scope on the color mosaic system is used.

However, in the light source device capable of providing illumination light suitable for any and all of the conventional rigid endoscopes, fiberscopes, and electronic scopes on the color mosaic and field sequential systems at least two of the infrared reflecting interference filter and the infrared absorbing filter have been used to block almost completely light in the infrared region. When the electronic scope on the field sequential system is employed, light in the infrared region has been removed in excess of need.

Such excessive removal of light in the infrared region, as shown in FIG. 1, accompanies the removal of light in the visible region and reaches a considerable amount. This impairs brightness required for illumination light. Also, removing light in the entire infrared region by using interference filters alone to improve the brightness is expensive and therefore unprofitable.

SUMMARY OF THE INVENTION

It is, therefore, an object of the present invention to provide a light source device for endoscopes which is capable of providing illumination light suitable for any of a rigid endoscope, fiberscope, electronic scope on the color mosaic system, or electronic scope on the field sequential system, so that the problems of breaking the infrared absorbing filter and of burning the fiber end of the light guide are solved and brightness for the illumination light is sufficient even when the electronic scope on the field sequential system is used.

According to one aspect of the present invention, the light source device for endoscopes is provided with a light source for emitting white light containing the components of light belonging to visible and infrared regions; a color separating filter on the field sequential system; and an infrared cutoff filter for blocking light in the infrared region within the wavelength range of the white light. When the color separating filter is placed in an optical path between the light source and the light guide, an interference filter in which an interference film is applied to its transparent base plate is disposed in the optical path.

Further, the light source device of the present invention is designed so that when the color separating filter is disposed in the optical path, the infrared cutoff filter includes an interference filter unit in which an interference film is applied to a transparent base plate, while when the color separating filter is not disposed in the optical path, the infrared cutoff filter includes at least an interference filter unit and an infrared absorbing filter unit for absorbing light having wavelengths in the infrared region. (The qualifier "unit" is used in the ordinary sense to indicate the referenced entity can also have a substructure. See the fourth embodiment for one such example.)

Still further, in the light source device of the present invention, it is desirable that means for decreasing the amount of light incident on the light guide is disposed in the infrared cutoff filter, or on the light source side of the infrared cutoff filter.

The light source device of the present invention is provided with a light source for emitting white light containing the components of light belonging to visible and infrared regions; a color separating filter on the field sequential system; and an infrared cutoff filter for blocking light in the infrared region within the wavelength range of the white light, wherein when the color separating filter is placed in an optical path between the light source and the light guide, a filter unit disposed in the optical path transmits light with wavelengths longer than 1100 nm, while when the color separating filter is not disposed in the optical path, the total spectral transmittance of light of the filter unit disposed in the optical path is arranged such that light with wavelengths longer than 1100 nm is sufficiently removed.

The light source device of the present invention is constructed as mentioned above, and thus when the rigid endoscope, fiberscope, or electronic scope on the color mosaic system is used, defects such as burning the fiber end of the light guide and breakage of the infrared absorbing filter do not develop, and sufficient brightness for illumination light is obtained. When the electronic scope on the field sequential system is used, white light containing components of light in the visible and infrared regions is filtered such that at least one part of the components of light in the infrared region is removed by the interference filter unit and the remaining components in the infrared region and components with wavelengths shorter than and in a range of the visible wavelength region are transmitted therethrough. R, G, and B components are sequentially separated from the visible light which has passed through the interference filter unit, by the color separating filter on the field sequential system, and are concentrated at the fiber end of the light guide. In this case, although a part of the infrared light remains, the fiber end of the light guide is not burned because the energy density of the visible light at the fiber end of the light guide is reduced to nearly ⅓ compared with the case where the rigid endoscope, fiberscope, or electronic scope on the color mosaic system is used. Since only the interference filter is used to remove the infrared light, a decrease in the amount of visible light can be kept to a minimum.

According to another aspect of the present invention, the light source device for endoscopes is constructed so that light emitted from the illumination light source is concentrated at the entrance end of the light guide by a condenser lens. At least two transmissive wavelength selecting filters are arranged between the illumination light source and the entrance end of the light guide to remove light with wavelengths less than 400 nm and more than 750 nm.

Further, in the light source device of the present invention constructed as in the foregoing, infrared light with wavelength components of at least 750 nm that is transmitted through a filter disposed closer to the illumination light source, of the transmissive wavelength selecting filters, has an amount of energy that satisfies $$P \times \left\{ \int_\lambda R(\lambda)T(\lambda)d\lambda \Big/ \int_\lambda R(\lambda)d\lambda \right\} < 60 \qquad (1)$$

where $R(\lambda)$ is the spectral energy emissivity of light with a wavelength $\lambda$ that is emitted from the illumination light source, $T(\lambda)$ is the spectral transmittance of the transmissive wavelength selecting filter disposed closer to the illumination light source for the wavelength $\lambda$, and P is the consumption power of a lamp used in the illumination light source. The integration with respect to wavelength $\lambda$ in Condition (1) is calculated over a wavelength range whose lower limit is 750 nm.

According to the light source device for endoscopes of the present invention, at least two transmissive wavelength selecting filters are arranged between the illumination light source and the entrance end of the light guide to remove light with wavelengths less than 400 nm and more than 750 nm, and thereby the burning of the entrance end of the light guide can be completely prevented. Specifically, since light with wavelengths longer than 750 nm belonging to the infrared region is blocked by the transmissive wavelength selecting filters and is not concentrated at the entrance end of the light guide, the entrance end of the light guide is prevented from being exposed to the heat of high temperature and from being burned. Furthermore, light with wavelengths less than 400 nm in the ultraviolet region is also blocked by the transmissive wavelength selecting filters, and thus even though an adhesive used to bond the fiber bundle of the light guide is of the type of absorbing ultraviolet light, the entrance end of the light guide will not be burned.

The filter disposed closer to the illumination light source has the property of practically blocking at least light (infrared) in a wavelength range of 750–1100 nm. Hence, where the transmissive wavelength selecting filters are constructed, in order from the light source side, with a first filter having the properties of transmitting light in a wanted wavelength region and of reflecting light in an unwanted wavelength region and a second filter having the properties of transmitting light in a wanted wavelength region and of absorbing light in an unwanted wavelength region, it is avoided that the second filter absorbs infrared light in the above wavelength range to generate heat and that the filter itself becomes a new infrared radiation source to burn the entrance end of the light guide. Moreover, it is also avoided that the second filter reaches a high temperature because of its heat generation and is deformed and broken by thermal expansion.

If each transmissive wavelength selecting filter has properties of transmitting light in a wanted wavelength region and of reflecting light in an unwanted wavelength region, it is avoidable that the filters absorb infrared light to generate heat. Consequently, the filters themselves can be prevented from becoming new infrared radiation sources that burn the entrance end of the light guide and break the filter due to thermal expansion.

Various types of lamps, including a xenon lamp and a halogen lamp, are used as illumination light sources for endoscopes. The spectral energy emissivity distribution of light radiated from each of these lamps has an inherent characteristic. If lamps identical in type are used and the consumption powers of the lamps vary, the amounts of emission energy of light radiated from the lamps will also vary. Hence, in the light source device of the present invention which comprises at least two transmissive wavelength selecting filters, it is desirable that the amount of energy of infrared light transmitted through a filter disposed closer to the illumination light source of the transmissive wavelength selecting filters satisfies Condition (1).

In Condition (1), the value of the denominator of the fraction in braces on the left side is proportional to the amount of energy of infrared light with wavelengths more than 750 nm emitted from the illumination light source, and the value of the numerator is proportional to the amount of infrared light with wavelengths more than 750 nm transmitted through the transmissive wavelength selecting filter disposed closer to the illumination light source. Thus, the fraction in braces on the left side of Condition (1) represents the ratio of the amount of energy of infrared light transmitted through the transmissive wavelength selecting filter disposed closer to the illumination light source to that of infrared light emitted from disposed closer to the illumination light source. Also, if the consumption power values of lamps used in the illumination light sources vary, the amounts of energy of infrared light emitted from the illumination light sources will also vary. For example, the amount of energy of infrared light emitted from the illumination light source using a lamp of consumption power 300 W is greater than that of infrared light emitted from the illumination light source using a lamp of consumption power 150 W. Therefore, in the left side of Condition (1) the energy ratio expressed by the fraction in braces is multiplied by the consumption power P of the lamp used in the illumination light source to yield the amount of energy of infrared light transmitted through the filter disposed closer to the illumination light source.

If the amount of energy of infrared light transmitted through the transmissive wavelength selecting filter disposed closer to the illumination light source fails to satisfy Condition (1), the amount of energy of infrared light reaching the other filter placed behind the closer filter becomes excessive, and the other filter breaks or becomes a new infrared radiation source to burn the entrance end of the light guide.

This and other objects as well as the features and advantages of the present invention will become apparent from the following detailed description of the preferred embodiments when taken in conjunction with the accompanying drawings.

DETAILED DESCRIPTION OF THE PREFERRED EMBODIMENTS

Figure 1:
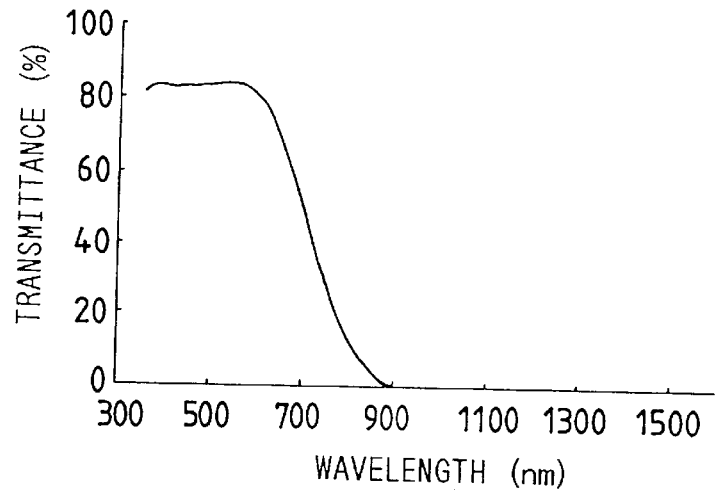
FIG. 1 is a view showing the spectral transmittance characteristic of an infrared absorbing filter used in a common light source for endoscopes.
Figure 2:
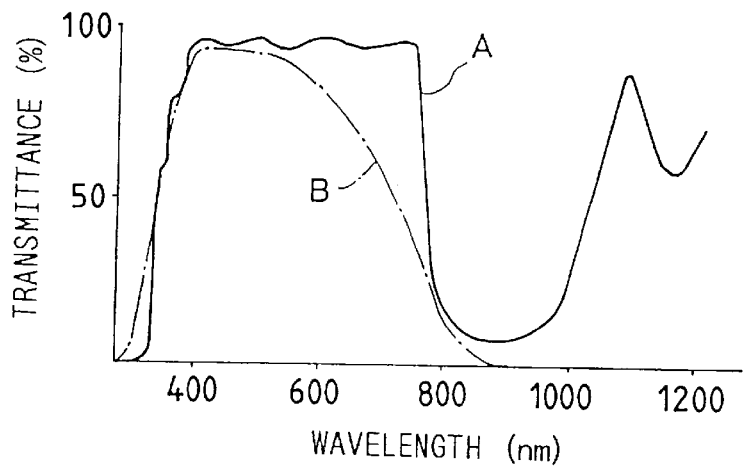
FIG. 2 is a view showing spectral transmittance characteristics of an infrared reflecting filter and an infrared absorbing filter of prior art.
Figure 3:
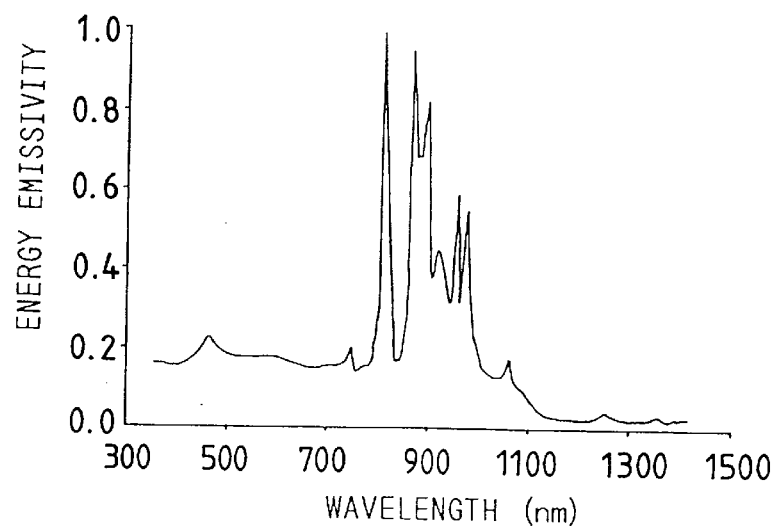
FIG. 3 is a view showing the spectral energy emissivity characteristic of a common xenon lamp.

In accordance with the embodiments shown in the drawings, the present invention will be explained in detail below.

First embodiment

Figure 4A:
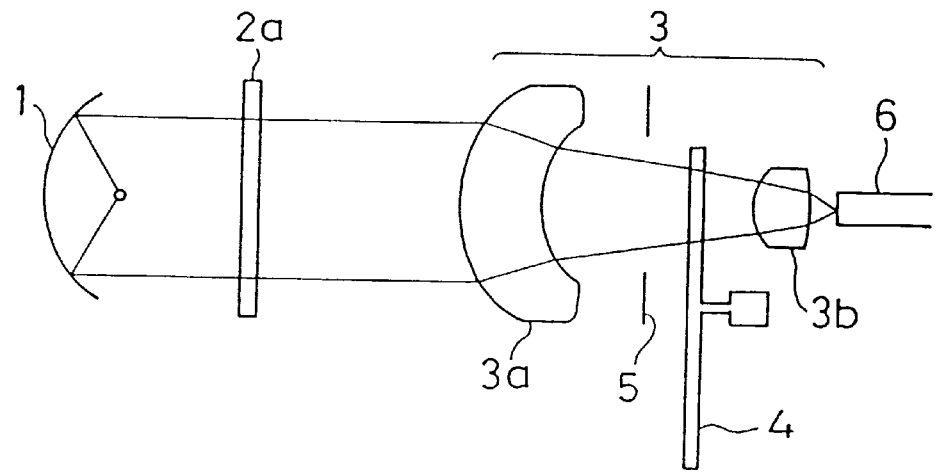
FIGS. 4A and 4B are views showing optical arrangements of a first embodiment of the light source device for endoscopes according to the present invention.

In the light source device of this embodiment, where an electronic scope on the field sequential system is used, as shown in FIG. 4A, an infrared reflecting interference filter 2a is interposed between a light source 1 and a condenser lens system 3, and a light guide 6 is disposed behind the condenser lens system 3. The condenser lens system 3 is composed of a front lens unit 3a and a rear lens unit 3b, each having a positive refracting power. A rotary color separating filter 4 on the field sequential system and a stop mechanism 5 as means for adjusting the amount of transmitted light are arranged between the front lens unit 3a and the rear lens unit 3b of the condenser lens system 3.

Figure 4B:
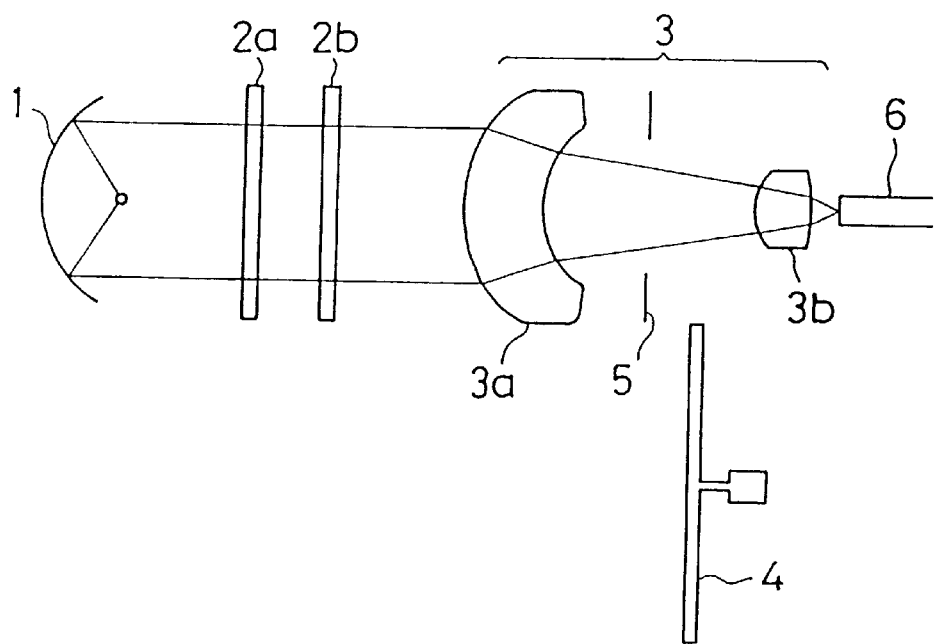

On the other hand, where a rigid endoscope, fiberscope, or electronic scope on the color mosaic system is used, as shown in FIG. 4B, an infrared absorbing filter 2b is inserted, in addition to the arrangement shown in FIG. 4A, between the interference filter 2a and the condenser lens system 3, and the rotary color separating filter 4 disposed between the front lens unit 3a and the rear lens unit 3b of the condenser lens system 3 is removed.

The device of the first embodiment is such that a drive, such as a motor, not shown, is mounted to drive the infrared absorbing filter 2a and the rotary color separating filter 4 on the field sequential system.

The device of the first embodiment, as mentioned above, is constructed so that the rotary color separating filter 4 on the field sequential system and the infrared absorbing filter 2b are movable in and out of the optical path, according to the type of the scope used. Hence, when the rigid endoscope, fiberscope, or electronic scope on the color mosaic system is used, the fiber end of the light guide 6 will not be burned, and even with the electronic scope on the field sequential system, brightness of illumination light can be improved.

Figure 5:
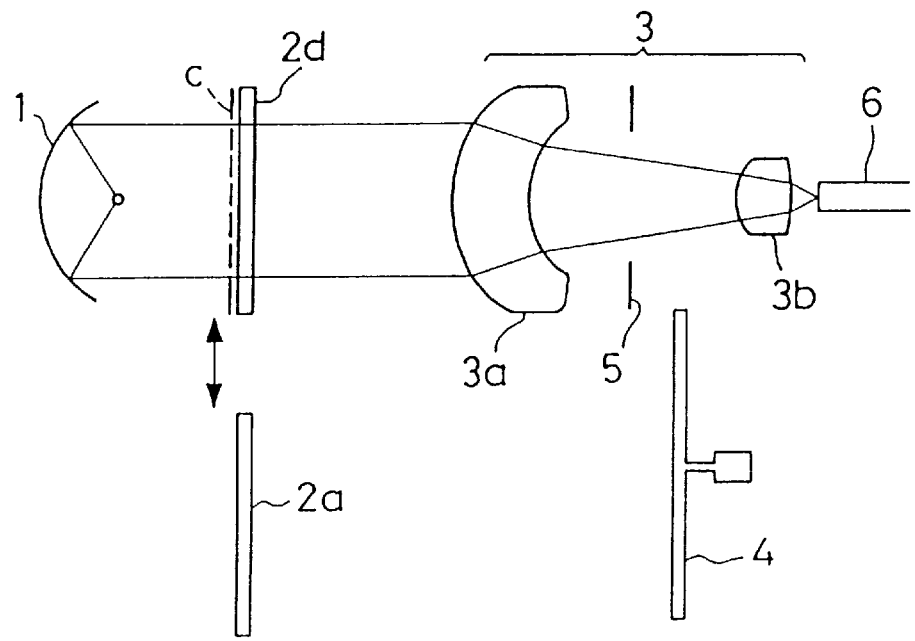
FIG. 5 is a view showing the arrangement of another example of the first embodiment.

In the first embodiment, filters to be replaced may be designed as follows: Where the electronic scope on the field sequential system is used, as shown in FIG. 4A, the infrared reflecting interference filter 2a is disposed. However, where the rigid endoscope, fiberscope, or electronic scope on the color mosaic system is used, an arrangement is made as shown in FIG. 5. Specifically, instead of the interference filter 2a and the infrared absorbing filter 2b shown in FIG. 4B, a filter 2d is used in which a multilayered film c of interference type for reflecting infrared light is evaporated on a surface directed to the light source 1.

In this arrangement also, the same effect as in FIGS. 4A and 4B can be secured. Moreover, space required for placing the filter is smaller than in FIGS. 4A and 4B, and thus the compactness of the light source device is facilitated.

Figure 6:
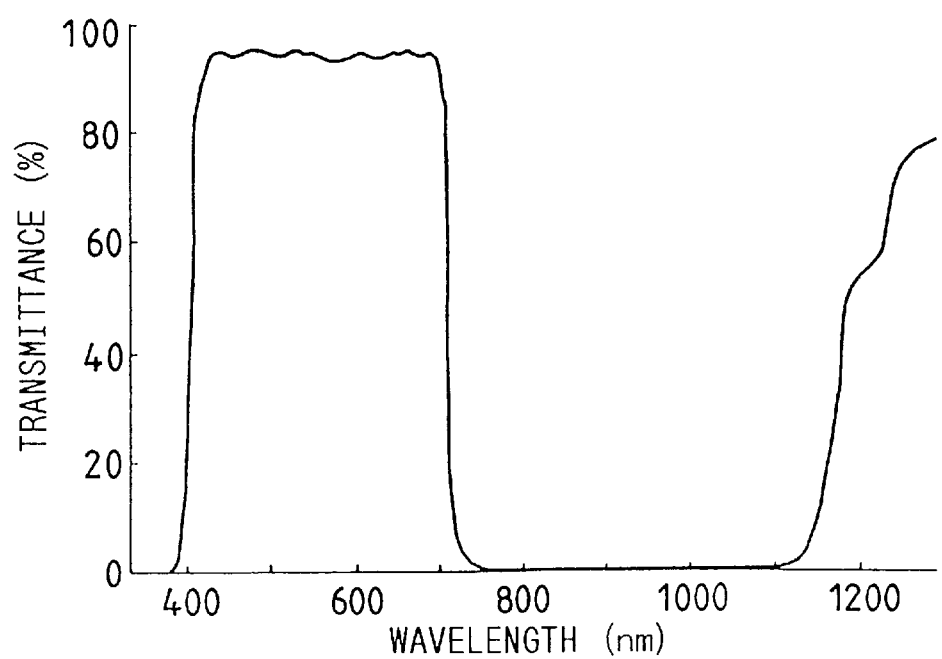
FIG. 6 is a view showing the transmittance characteristic of an infrared reflecting interference filter used in the first embodiment.
Figure 7A:
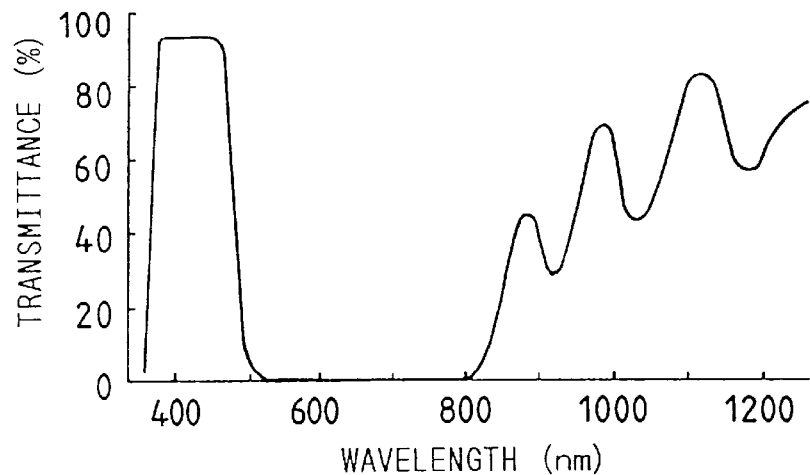
FIGS. 7A, 7B, and 7C are views showing transmittance characteristics of B (blue), G (green), and R (red) transmitting filters, respectively, in a rotary color separating filter of a field sequential system used in the first embodiment.
Figure 7B:
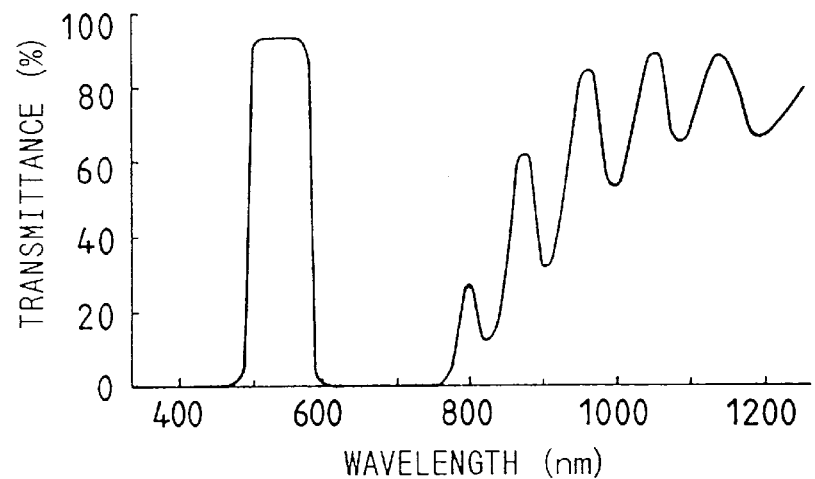
Figure 7C:
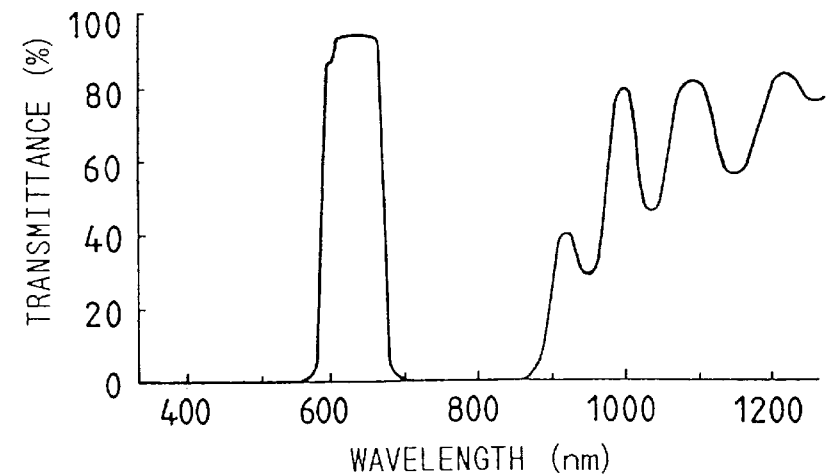
Figure 8A:
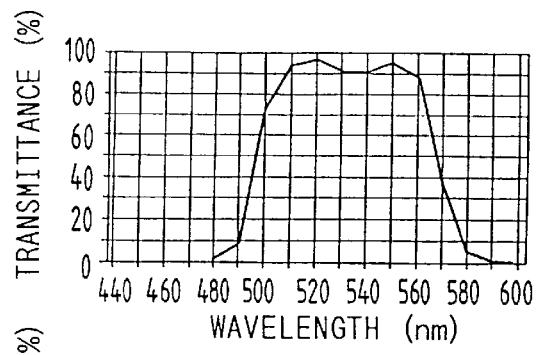
FIGS. 8A, 8B, 8C, 8D, and 8E are views showing transmittance characteristics where an angle of incidence of light on the interference film of a G light transmitting filter is changed.
Figure 8B:
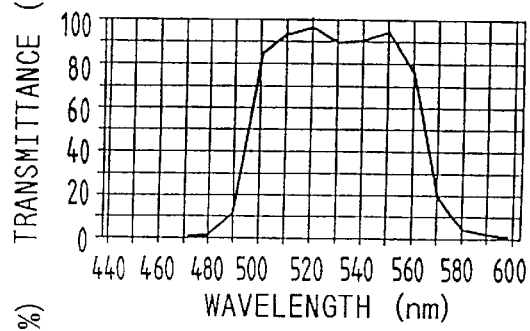
Figure 8C:
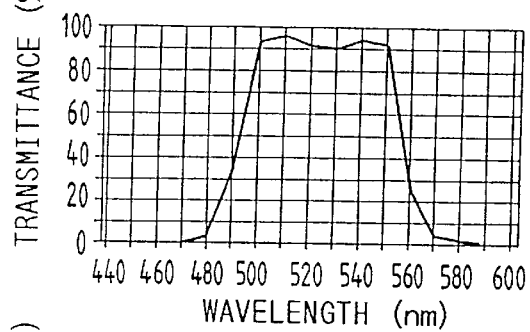
Figure 8D:
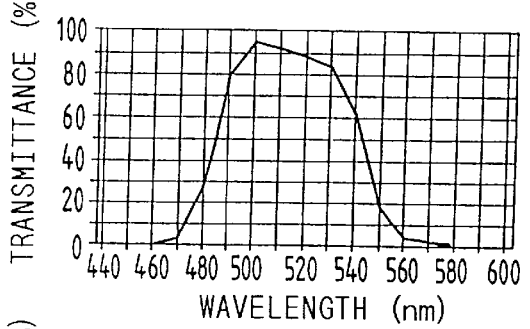
Figure 8E:
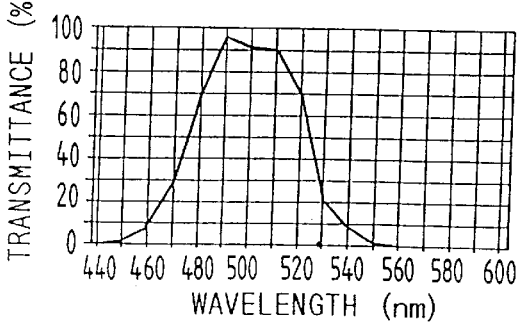

FIG. 6 is a curve diagram showing the transmittance characteristic of the infrared reflecting interference filter 2a used in the first embodiment. When the rigid endoscope, fiberscope, or electronic scope on the color mosaic system is used, the infrared reflecting interference filter 2a is used for the purpose of preventing the breakage, such as cracking due to heat, of the infrared absorbing filter 2b. When the electronic scope on the field sequential system is employed, the infrared absorbing filter 2b is not disposed in the optical path, and thus the infrared reflecting interference filter 2a serves to obviate not only the burning of the fiber end of the light guide, but also the degradation of an image. In this way, it is required that the infrared reflecting interference filter 2a eliminates light in the wavelength range which will be described below. It is necessary that the wavelength range of light removed by the infrared reflecting interference filter 2a does not overlap, at its short-wavelength side end, with the visible region of light to be transmitted through the rotary color separating filter 4 on the field sequential system. On the other hand, a solidstate image sensor used in electronic scopes has sensitivity in a wide range to infrared light, and thus unless light with wavelengths in the infrared region to which the solidstate image sensor has sensitivity is removed, the image by the electronic scope on the field sequential system will be deteriorated. Therefore, the wavelength range of light removed by the infrared reflecting interference filter 2a is required to reach, at its long-wavelength end, at least to a wavelength of light in the infrared region to which the solidstate image sensor has sensitivity. FIGS. 7A–7C show the relationships between the wavelength of light and the spectral transmittance of B (blue), G (green), and R (red) transmitting filters, respectively, in the rotary color separating filter on the field sequential system used in the first embodiment. In the wavelength range of light to be principally transmitted by the R transmitting filter in the rotary color separating filter 4 on the field sequential system (i.e., R light region), the limit of the wavelength at which the transmittance becomes 5% is about 680 nm. The long-wavelength side limit of the wavelength range of light to which the solid state image sensor has sensitivity is about 1100 nm. It is therefore favorable that the wavelength range such that the transmittance of infrared light by the infrared reflecting interference filter 2a is kept at 5% or less is from about 750 through at least 1100 nm, whereby when the rigid endoscope, fiberscope, or electric scope on the color mosaic system is used, the thermal load on the infrared absorbing filter 2b caused by infrared light is relieved, while when the electronic scope on the field sequential system is used, the degradation of the image attributable to the infrared light is prevented without attenuation of R light.

If, however, the wavelength of light to be cut on the long wavelength side by the R transmitting filter in the electronic scope on the field sequential system is increased, a wavelength of 800 nm will suffice for the lower limit (shortest) wavelength of light to be cut by the filter 2a. If, for example, the light source 1 is a xenon lamp and design is made so that at least light in a wavelength range of 800–1000 nm can be blocked, it has practical use in view of its spectral characteristic.

As mentioned above, the wavelength range of incident light to be blocked on the infrared reflecting interference filter 2a is set so that when the rigid endoscope, fiberscope, or electronic scope on the color mosaic system is used a defect, such as breakage of the infrared absorbing filter 2b, does not develop. In addition, when the electronic scope on the field sequential system is used, attenuation of R light and degradation of the image attributable to infrared light do not occur.

Specifically, the light source device of the first embodiment includes a light source for emitting white light containing the components of light belonging to visible and infrared regions, and at least a color separating filter of the field sequential system and an infrared cutoff filter for blocking light in the infrared region within the wavelength range of the white light. When the color separating filter is placed in the optical path between the light source and the light guide, the filter unit disposed in the optical path transmits light having wavelengths of 100 nm or more in terms of the total spectral transmittance. In contrast to this, when the color separating filter is not placed in the optical path, the filter unit completely removes light having wavelengths of 100 nm or more. All or part of the filter unit is replaceable.

The device of the first embodiment, which is constructed as mentioned above, solves the problems of the prior art, so that when the rigid endoscope, fiberscope, or electronic scope on the color mosaic system is used, the fiber end of the light guide is not burned, while even when the electronic scope on the field sequential system is used, brightness as illumination light is sufficiently secured.

For the positions of the filters in the first embodiment, it is best that the interference filter is placed so that an angle of incidence of light is 0°. As the angle of incidence of light on the filter is increased, the performance of the filter degrades. Hence, it is favorable that the infrared reflecting interference filter 2a is disposed in a parallel beam between the light source 1 and the condenser lens system 3. In order to fully exhibit the performance of the rotary separating filter 4 on the field sequential system, it is desirable that the filter 4 is placed in a parallel beam between the light source 1 and the condenser lens system 3. In this case, however, if the beam diameter is large, the rotary color separating filter 4 must also be made large. If the rotary color separating filter 4 is large sized, considerable strength will be required for the filter. Furthermore, a motor for driving the filter need be made oversize and powerful. This raises cost and highly increases the weight of the device itself.

If the rotary color separating filter 4 on the field sequential system is disposed between the condenser lens system 3 and the light guide 6, the filter is allowed to be small and a driving motor with low torque is applicable to the filter. In this case, however, the transmittance of light of the rotary color separating filter 4 on the field sequential system is lowered, and color reproduction is deteriorated, with the result that the object cannot be faithfully displayed with color. This does not provide good practical use.

If, however, the angle of incidence of light on the rotary color separating filter 4 is 20° or less, the deterioration of the transmittance characteristic of light is not very high, and a faithful color display of the object is possible. FIGS. 8A–8E show the changes of the transmittance characteristics of light with respect to the variations of the angles of incidence of light on the interference film of the G light transmitting filter which has the properties of transmitting only light in the wavelength range of G light and of reflecting light in the other wavelength range. In this case, the central wavelength range of G light set in the G light transmitting filter is 510–560 nm, and it is seen from these figures that if the angle of incidence of light exceeds 20°, the transmittance characteristic of light in the central portion of the G-light region will be considerably lowered.

Thus, in the first embodiment, as shown in FIG. 4A, the condenser lens system 3 is constructed with two lens units of the front lens unit 3a and the rear lens unit 3b, and the rotary color separating filter 4 on the field sequential system is interposed therebetween. The front lens unit 3a is designed so that a parallel beam can be concentrated to such an extent that the transmittance of light through the rotary color separating filter 4 is not deteriorated. In this way, by placing the rotary color separating filter 4 between the front lens unit 3a and the rear lens unit 3b, the filter is made small in size and sufficient transmittance characteristics of light can be maintained.

Where the rigid endoscope, fiberscope, or electronic scope on the color mosaic system is used, it is required that the infrared absorbing filter 2b is inserted in the optical path of the light source device and is disposed between the interference filter 2a and the condenser lens system 3. This is because if the infrared absorbing filter 2b is placed at a light gathering position behind the condenser lens system 3 or in front of the interference filter 2a, the filter 2b may be broken.

Where the rigid endoscope, fiberscope, or electronic scope on the color mosaic system is used, white light emitted from the light source 1 is not separated into R, G, and B, but is concentrated at the fiber end of the light guide by the condenser lens system 3. In this case, unlike the case of the use of the electronic scope on the field sequential system, it is necessary to almost completely remove light in the infrared region from the white light emitted from the light source 1. For this purpose, the infrared reflecting interference filter 2a must be used in combination with the infrared absorbing filter 2b.

The transmittance characteristic of light of the infrared absorbing filter 2b is as shown in FIG. 1. It is seen from this figure that the infrared absorbing filter 2b almost completely cuts out light in the infrared region. Thus, there is no defect of burning the fiber end of the light guide 6.

Second embodiment

Figure 9A:
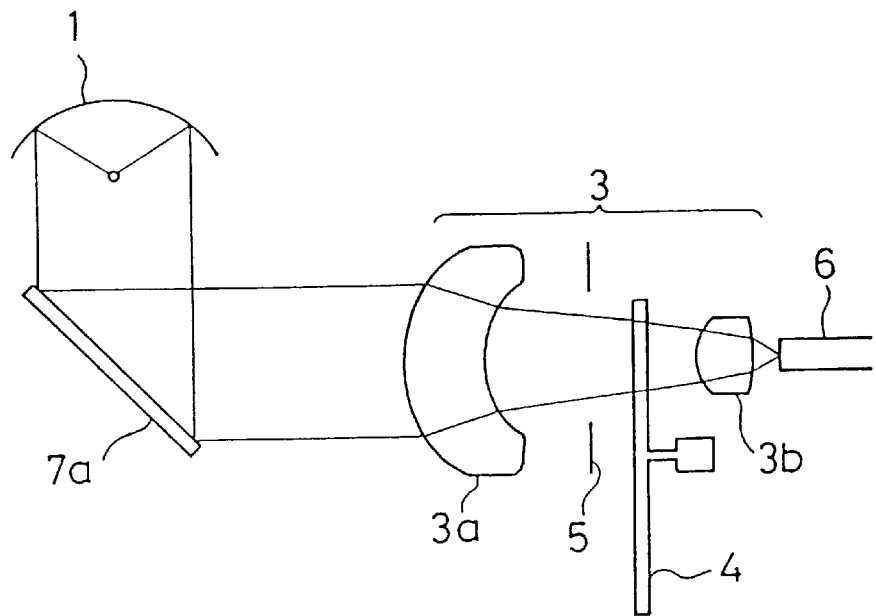
FIGS. 9A and 9B are views showing optical arrangements of a second embodiment of the light source device for endoscopes according to the present invention.
Figure 9B:
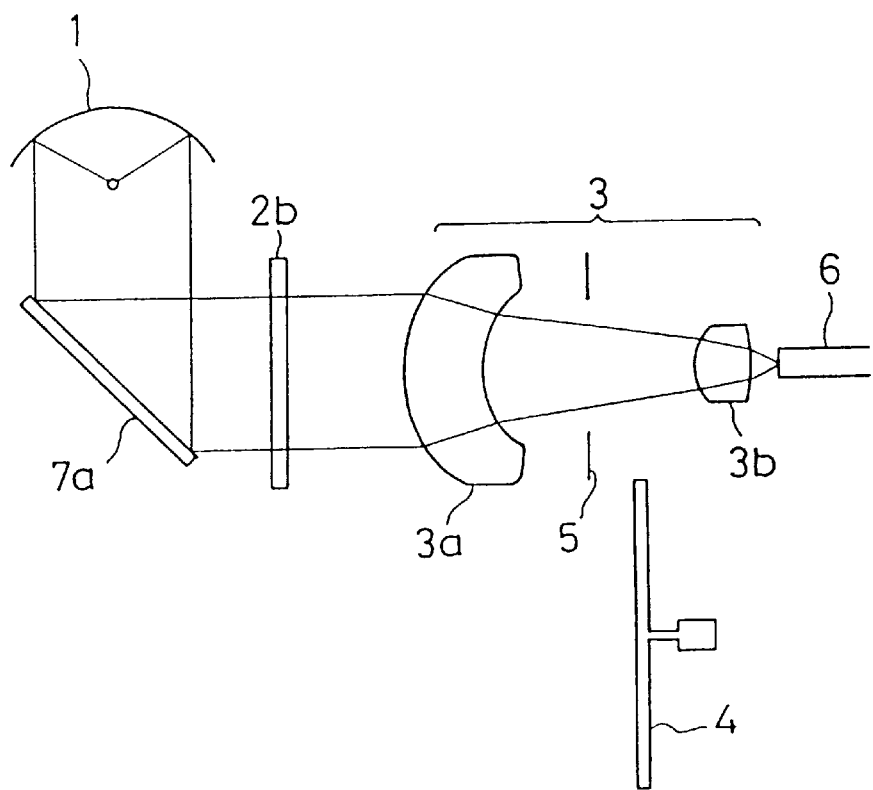

In this embodiment, where the electronic scope on the field sequential system is employed, an arrangement is made as shown in FIG. 9A. Specifically, an infrared transmitting interference filter 7a is disposed so that light emitted from the light source 1 can be reflected toward the condenser lens system 3. The infrared transmitting interference filter 7a is situated so that the normal to the filter makes an angle of 45° with incident light, and has the functions of transmitting light in the infrared region and of reflecting light in the visible region. With the exception of the light source 1 and the infrared transmitting interference filter 7a, the arrangement is the same as in the first embodiment (refer to FIG. 4A) with respect to the condenser lens system 3, the rotary color separating filter 4 on the field sequential system, the stop mechanism 5, and the light guide 6.

Where the rigid endoscope, fiberscope, or electronic scope on the color mosaic system is employed, as shown in FIG. 9B, the infrared absorbing filter 2b is inserted in the optical path between the infrared transmitting interference filter 7a and the condenser lens system 3, and the rotary color separating filter 4 on the field sequential system situated between the front lens unit 3a and the rear lens unit 3b of the condenser lens system 3 is removed.

In the second embodiment also, like the first embodiment, a drive, such as a motor, not shown, is provided to drive the infrared absorbing filter 2b and the rotary color separating filter 4.

The light source device for endoscopes in the second embodiment is constructed as mentioned above, and when the electronic scope on the field sequential system is used, brightness of illumination light can be improved as in the first embodiment. Even when the rigid endoscope, fiberscope, or electronic scope on the color mosaic system is used, breakage of the infrared absorbing filter or burning of the fiber end of the light guide will not occur, and stable illumination light can be provided.

With the device of the first embodiment, which uses the infrared reflecting interference filter, there is the fear that light in the infrared region is reflected back toward the light source to cause damage to the light source itself. However, since the device of the second embodiment uses the infrared transmitting interference filter, light in the infrared region is not reflected back toward the light source, and thus does not cause damage to the light source. The second embodiment is superior in this respect to the first embodiment.

Third embodiment

Figure 10A:
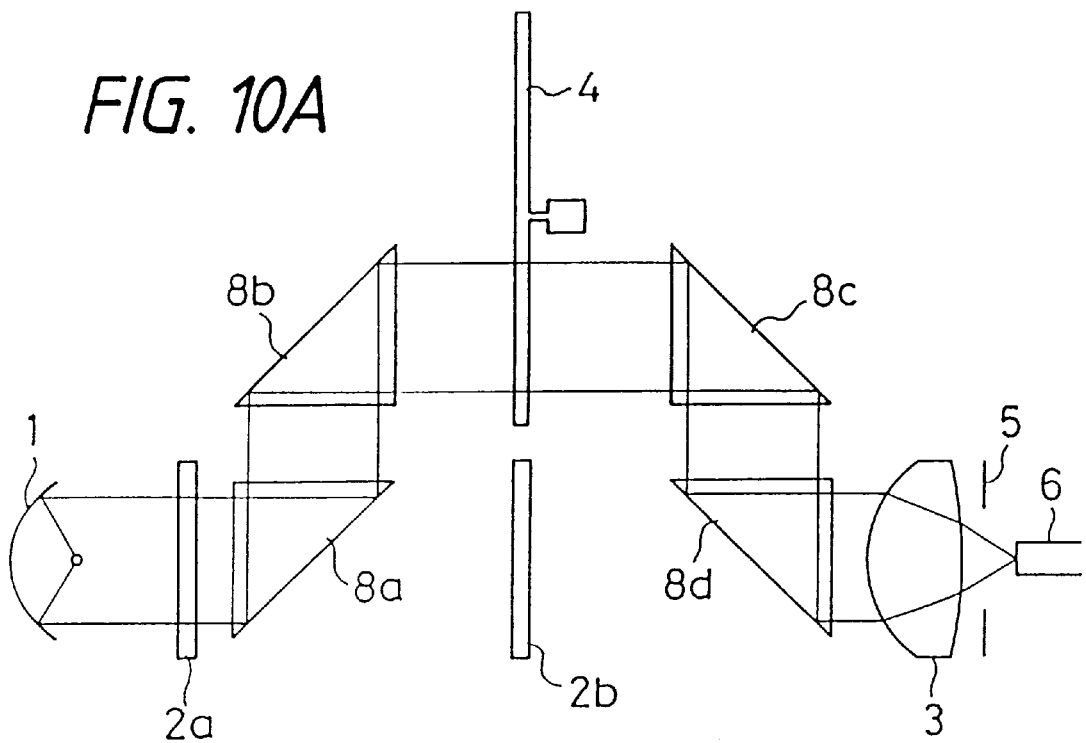
FIGS. 10A and 10B are views showing optical arrangements of a third embodiment of the light source device for endoscopes according to the present invention.
Figure 10B:
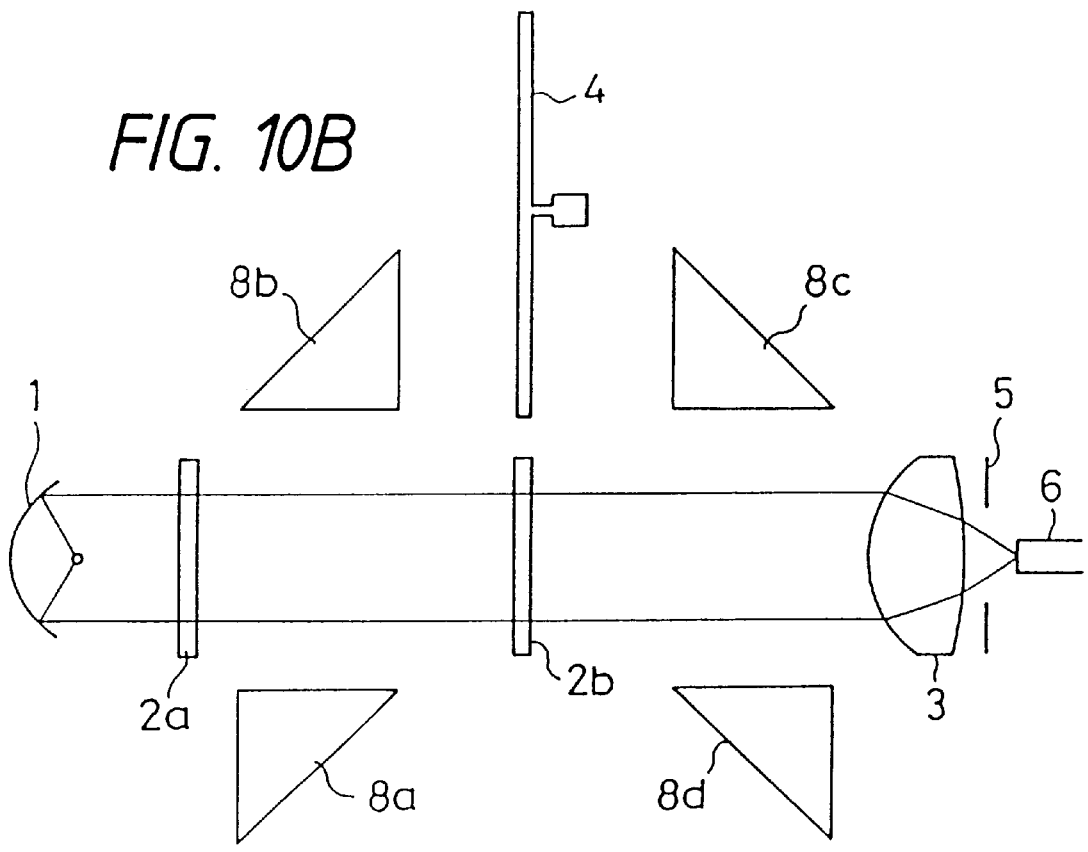
Figure 11A:
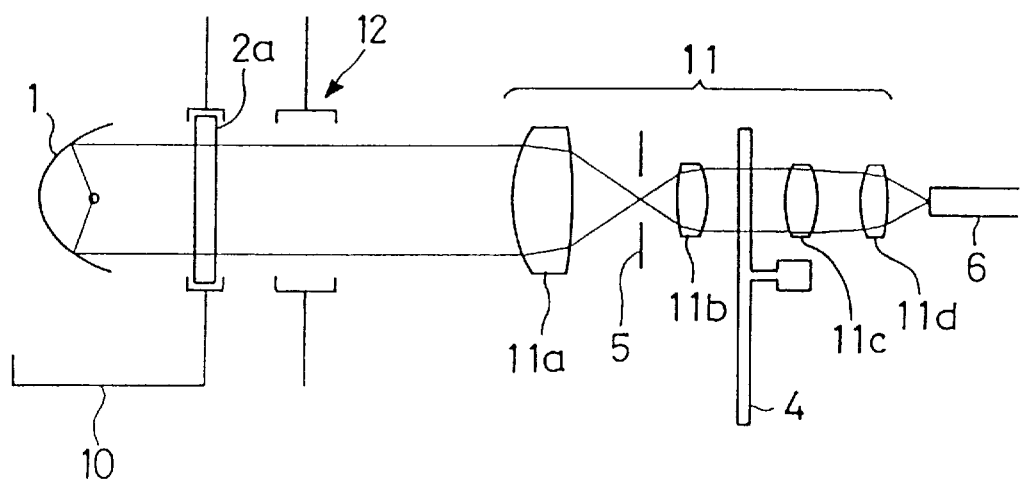
FIGS. 11A and 11B are views showing optical arrangements of a fourth embodiment of the light source device for endoscopes according to the present invention.
Figure 11B:
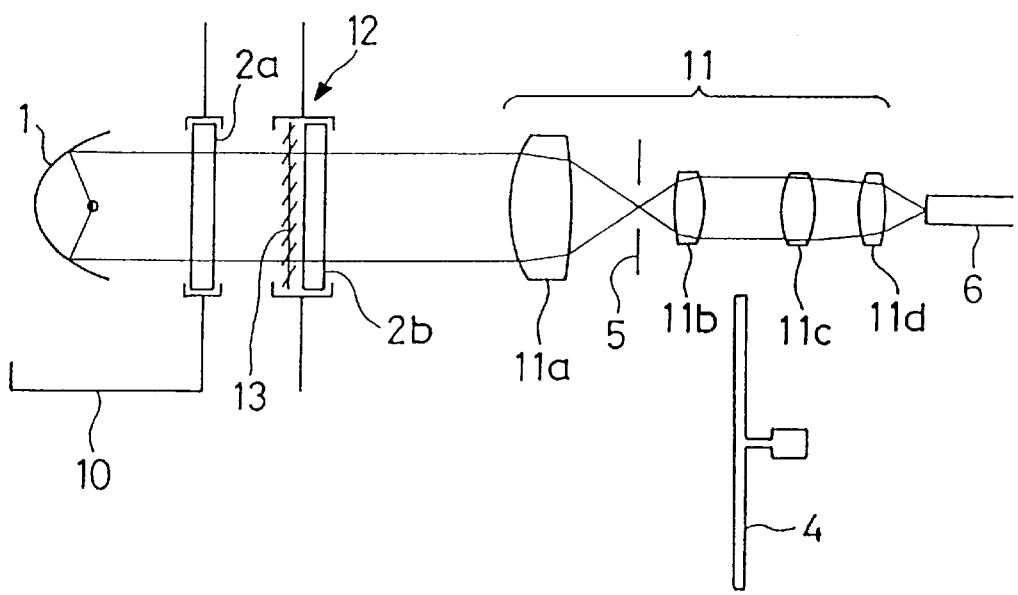

The light source device of this embodiment has arrangements shown in FIGS. 10A and 11B. Specifically, the infrared reflecting interference filter 2a and the infrared absorbing filter 2b are arranged in the optical path connecting the light source 1 with the condenser lens system 3 having a positive refracting power. A totally reflecting prism 8a is interposed between the filters 2a and 2b, and a totally reflecting prism ad between the filter 2b and the condenser lens system 3. Each of the totally reflecting prisms 8a and ad reflects incident light to change its direction by 90°. Each prism can be moved vertically from the position shown in FIG. 10A to that in FIG. 10B. On the upper side of the prisms 8a and ad, totally reflecting prisms 8b and 8c which are identical with the prisms 8a and ad are arranged, each reflecting incident light to change its direction by 90°. The rotary color separating filter 4 on the field sequential system is placed between the prisms 8b and 8c, the light guide 6 is disposed behind the condenser lens system 3, and the stop mechanism 5 as means for adjusting the amount of transmitted light is interposed between the condenser lens system 3 and the light guide 6.

Thus, in the third embodiment, where the electronic scope on the field sequential system is employed, as shown in FIG. 10A, light emitted from the light source 1 is incident on the infrared reflecting interference filter 2a, and thereby most of the components of light in the infrared region are eliminated.

Subsequently, the light follows the optical path in such a manner as to pass through the prisms 8a and 8b, the rotary color separating filter 4, and the prisms 8c and 8d and to enter the condenser lens system 3.

On the other hand, where the rigid endoscope, fiberscope, or electronic scope on the color mosaic system is used, as depicted in FIG. 10B, the prisms 8a and 8d are slid to deviate from the optical path. Light emitted from the light source 1 is incident on the infrared reflecting interference filter 2a, and thereby most of the components of light in the infrared region are removed. Subsequently, the light is incident on the infrared absorbing filter 2b, by which the components of light in the infrared region are completely eliminated, and then enters the condenser lens system 3.

The light source device for endoscopes in the third embodiment is constructed as mentioned above, and when the electronic scope on the field sequential system is used, as in the first and second embodiments, brightness of illumination light can be improved. Even when the rigid endoscope, fiberscope, or electronic scope on the color mosaic system is employed, as in the first and second embodiments, the defects, such as breakage of the infrared absorbing filter and burning of the fiber end of the light guide, will not occur.

In the first and second embodiments, when the electronic scope on the field sequential system is replaced with the rigid endoscope, fiberscope, or electronic scope on the color mosaic system, the infrared absorbing filter 2b and the rotary color separating filter 4 must be moved. In this way, to drive these filters, a large sized motor is required, thus raising cost and increasing the weight of the entire device. In the third embodiment, by contrast, only two small prisms are moved and a drive requires a small sized motor. Thus, a cost reduction and compact design of the device can be attained.

Fourth embodiment

The light source device of this embodiment uses means for attenuating light, such as a beam attenuation mesh, disposed in the optical path to accommodate the case where emergent light from the light source for use in the rigid endoscope, fiberscope, or electronic scope on the color mosaic system is considerably intense and the burn ing of the fiber end of the light guide is produced even when infrared light is almost completely removed so that only visible light remains.

In the fourth embodiment, where the electronic scope on the field sequential system is applied, as shown in FIG. 11A, the light source device is constructed with a lamp house 10 incorporating the light source 1 and the infrared reflecting interference filter 2a, a condenser lens system 11, and the light guide 6. Between the lamp house 10 and the condenser lens system 11 is placed a turret plate 12, whose optical path section empties so that a beam of light is not blocked. The condenser lens system 11 is composed of four positive lenses 11a, 11b, 11c, and 11d. The stop mechanism 5 as means for adjusting the amount of transmitted light is interposed between the positive lens 11a and the positive lens 11b, and the rotary color separating filter 4 on the field sequential system is placed between the positive lens 11b and the positive lens 11c.

On the other hand, where the rigid endoscope, fiberscope, or electronic scope on the color mosaic system is used, as shown in FIG. 11B, the turret plate 12 is rotated so that a beam attenuation mesh 13 and the infrared absorbing filter 2b are placed simultaneously in the optical path, and at the same time, the rotary color separating filter 4 is removed from the optical path. The beam attenuation mesh 13 is made of metal and mounted integral with the infrared absorbing filter 2b to the turret plate 12, and they are arranged in the order of the beam attenuation mesh 13 and the infrared absorbing filter 2b from the source side.

The light source device of the fourth embodiment is constructed as mentioned above, and when the electronic scope on the field sequential system is used, as in the first, second, and third embodiments, brightness of illumination light can be improved. Even when the rigid endoscope, fiberscope, or electronic scope on the color mosaic system is used, the breakage of the infrared absorbing filter or the burning of the fiber end of the light guide will not be caused, and stable illumination light can be provided.

The beam attenuation mesh 13 used in the fourth embodiment, which is interposed between the light source 1 and the infrared absorbing filter 2b, brings about the effect that not only is the fiber end of the light guide 6 protected, but also the amount of light absorbed by the infrared absorbing filter 2b is decreased. The thermal load on the infrared absorbing filter 2b is thus relieved, and thermal deformation and breakage can be obviated.

When the beam attenuation mesh 13 is placed in the optical path, however, the beam attenuation mesh 13 itself is heated to a considerably high temperature and generates heat. Although it is in general known that a heating element radiates infrared light, the beam attenuation mesh 13 is situated on the source side of the infrared absorbing filter 2b, and hence infrared light emanating from the heated beam attenuation mesh 13 will be eliminated.

Figure 12A:
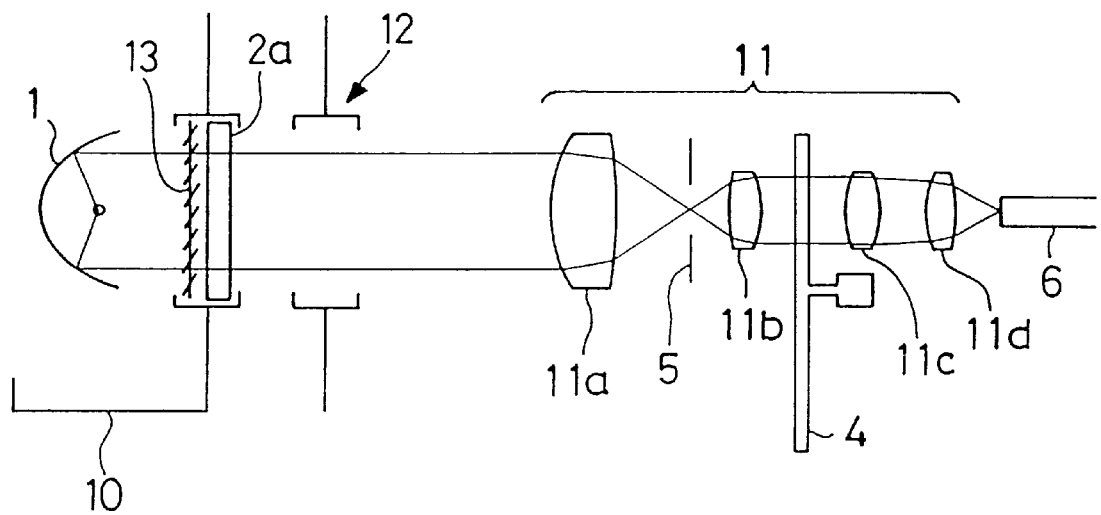
FIGS. 12A and 12B are views showing optical arrangements of another example in the fourth embodiment.
Figure 12B:
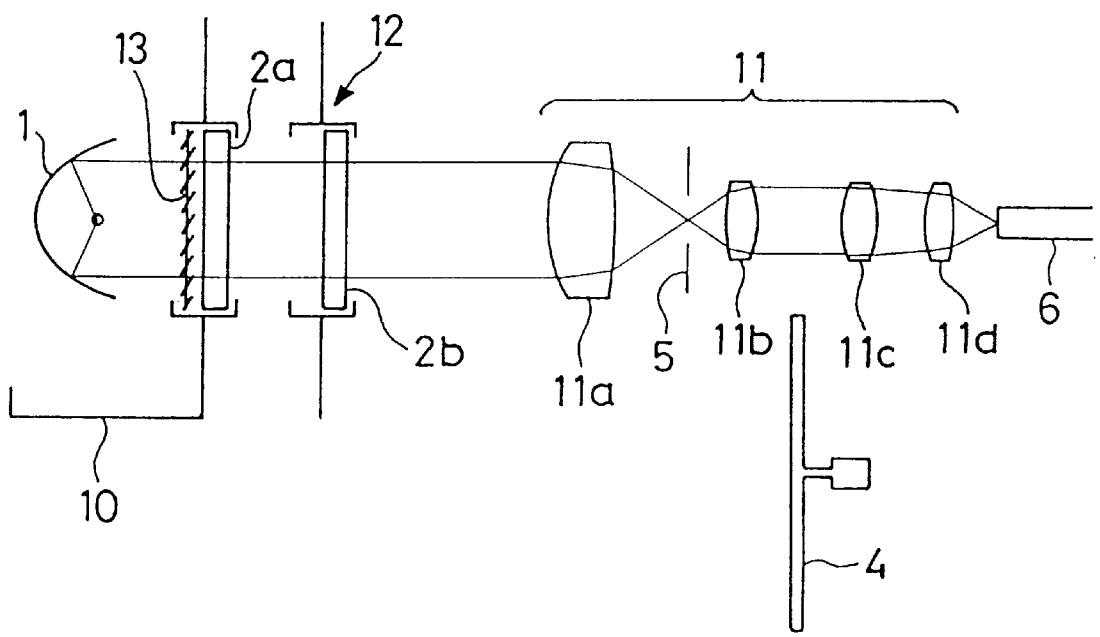

If the beam attenuation mesh 13 is placed on the condenser lens side of the infrared absorbing filter 2b, the thermal load on the infrared absorbing filter 2b cannot be relieved, and in addition, the light guide 6 will be heated by infrared light resulting from the heating of the beam attenuation mesh 13. This fails to bring about the effect that the beam attenuation mesh 13 is inserted in the optical path to protect the light guide, and thus is unfavorable.

Where the electronic scope on the field sequential system is applied and brightness of illumination light is sufficiently secured, the light source device of the fourth embodiment may be designed as depicted in FIGS. 12A and 12B. Specifically, with the use of the electronic scope on the field sequential system, as shown in FIG. 12A, the light source 1, the beam attenuation mesh 13, and the infrared reflecting interference filter 2a are arranged in the lamp house 10, and the optical path section of the turret plate 12 situated between the lamp house 10 and the condenser lens system 11 is empty so as not to block the light beam. The beam attenuation mesh 13, as in FIG. 11B, is made of metal. The beam attenuation mesh 13 and the infrared reflecting interference filter 2a are arranged in that order from the source side. The arrangement of the condenser lens system 11, the stop mechanism 5, the rotary color separating filter 4, and light guide 6 is the same as in FIG. 11A.

With the use of the rigid endoscope, fiberscope, or electronic scope on the color mosaic system, as shown in FIG. 12B, the turret plate 12 is rotated so that the infrared absorbing filter 2b is placed in the optical path, and at the same time, the rotary color separating filter 4 is removed from the optical path.

Even when the light source device is constructed as mentioned above, the same effect as in FIGS. 11A and 11B is secured, and protecting the fiber end of the light guide and the relief of the thermal load or the infrared absorbing filter 2b become possible. If the light source 1 emits intense light, and the interference filter is disposed adjacent to the light source 1, it is likely that the interference film of the filter will be degraded by the heat thus changing its interference characteristics. However, by placing the beam attenuation mesh 13 on the source side of the interference filter 2a, the amount of light incident on the interference filter 2a is decreased, and the interference film is protected.

Each filter used in the fourth embodiment has the same property as in the first, second, and third embodiments. The spectral transmittance characteristics of individual filters are thus the same as in FIG. 6 for the infrared reflecting interference filter 2a, FIG. 1 for the infrared absorbing filter 2b, and FIGS. 7A–7C for the rotary color separating filter 4 on the field sequential system.

In the fourth embodiment, the infrared reflecting interference filter 2a and the infrared absorbing filter 2b are each used but there may be a plurality of each of them. Also, although the beam attenuation mesh 13 made of metal is used as a means for attenuating light, another means, such as an ND filter, may be used to bring about the same effect. If the order of the mounting positions of the infrared cutoff filter and the means for attenuating light is the same as in the fourth embodiment, the same effect can be secured even though means other than the lamp house 10 and the turret plate 12 are used for setting the filters and the light attenuating means in place.

Fifth embodiment

Figure 13:
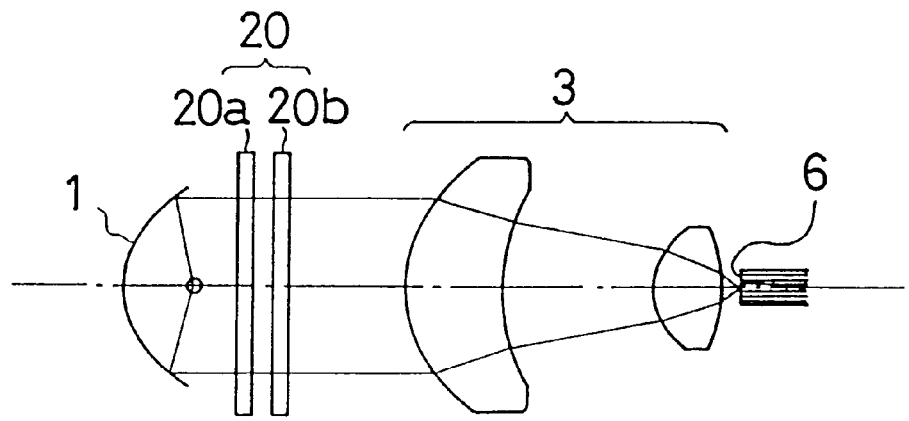
FIG. 13 is a view showing the optical arrangement of a fifth embodiment of the light source device for endoscopes according to the present invention.

In this embodiment, as shown in FIG. 13, a transmissive wavelength selecting filter unit 20 is comprised of two filters: in order from the source side, a reflecting filter 20a which is given a property of reflecting light with unwanted wavelengths by a multilayered interference film coated by evaporation on a transparent glass base plate and an absorbing filter 20b constructed of material that absorbs infrared light. The spectral transmittance characteristics of the reflecting filter 20a and the absorbing filter 20b are the same as those shown in FIGS. 6 and 1, respectively. Of light emitted from the light source 1, light (ultraviolet) with wavelengths less than 400 nm and light (infrared) with wavelengths 750–1100 nm are removed by the reflecting filter 20a. Subsequently, light (infrared) with wavelengths more than 1100 nm is eliminated by the absorbing filter 20b. In this way, ultraviolet and infrared light are separately removed by the reflecting filter 20a and the absorbing filter 20b, and thereby only light in the visible region is concentrated at the entrance end of the light guide 6. Since light (infrared) with wavelengths of 750–1100 nm is cut out by the reflecting filter 20a situated closer to the illumination light source 1 than the absorbing filter 20b, it is prevented from absorbing much infrared light in the above wavelength range so as to generate heat and become a new infrared radiation source which could cause the entrance end of the light guide 6 to burn or break by thermal expansion. The condenser lens system 3 is disposed between the transmissive wavelength selecting filter unit 20 and the entrance end of the light guide 6.

Moreover, ultraviolet light with wavelengths less than 400 nm is removed by the reflecting filter 20a, and even though an adhesive bonding the fiber bundle of the light guide is of the type that absorbs ultraviolet light, the entrance end of the light guide will not burn. Also, although the ultraviolet light with wavelengths less than 400 nm is cut out by the reflecting filter 20a, the multilayered interference film possessing the property of reflecting the ultraviolet light used for this purpose may be evaporated on the absorbing filter 20b in place of the reflecting filter 20a.

In the fifth embodiment, a xenon lamp with a consumption power of 300 W is used as the illumination light source. In this case, the value on the left side of Condition (1), which defines the amount of energy of infrared light with wavelengths more than 750 nm transmitted through the reflecting filter 20a, is 24.2, which satisfies Condition (1).

Sixth embodiment

Figure 14:
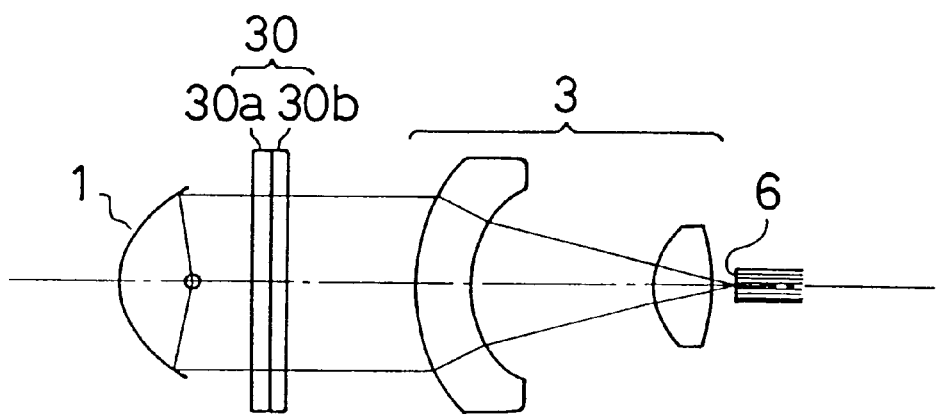
FIG. 14 is a view showing the optical arrangement of a sixth embodiment of the light source device for endoscopes according to the present invention.
Figure 15:
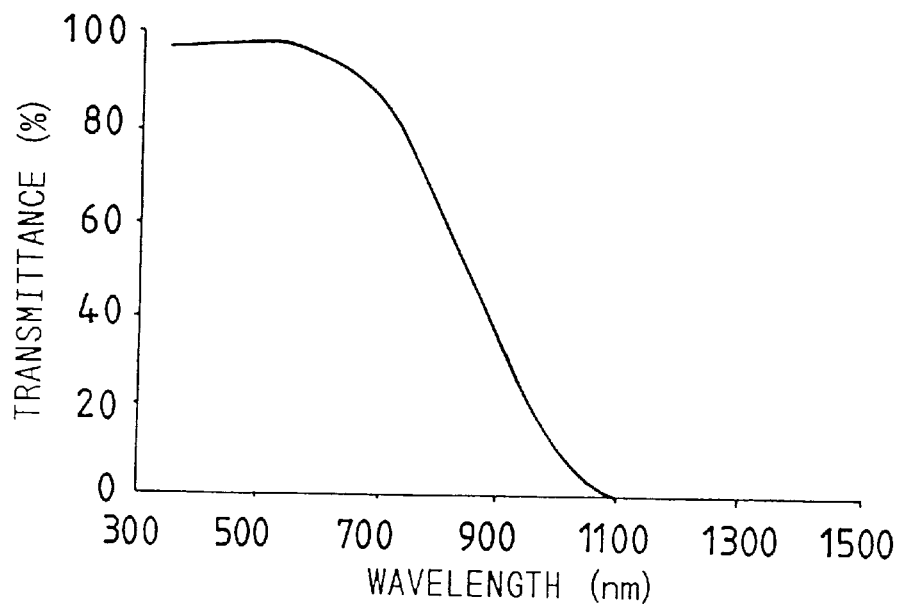
FIG. 15 is a view showing the spectral transmittance characteristic of a second reflecting filter used in the sixth embodiment.

In this embodiment, as shown in FIG. 14, a transmissive wavelength selecting filter unit 30 includes a combination of two reflecting filters, each being given the property of reflecting light with unwanted wavelengths by a multilayered interference film coated by evaporation on a transparent glass base plate. Of these two reflecting filters, a first reflecting filter 30a placed closer to the illumination light source 1 has the spectral transmittance characteristic shown in FIG. 6, and a second reflecting filter 30b has the spectral transmittance characteristic shown in FIG. 15. Light emitted from the illumination light source 1 is filtered such that light (ultraviolet) with wavelengths less than 400 nm and light (infrared) with wavelengths 750–1100 nm are removed by the first reflecting filter 30a. Subsequently, light (infrared) with wavelengths more than 1100 nm is eliminated by the second reflecting filter 30b, and thereby only light in the visible region is concentrated at the entrance end of the light guide 6. Also, the condenser lens system 3 is interposed between the transmissive wavelength selecting filter unit 30 and the entrance end of the light guide 6.

In this way, the second reflecting filter 30b is disposed behind the first reflecting filter 30a, and thereby it is avoidable that the filter unit absorbs infrared light to generate heat. It can thus be completely obviated that the filter unit itself becomes a new infrared radiation source to burn the entrance end of the light guide or to be broken due to thermal expansion. In the sixth embodiment, a xenon lamp with a consumption power of 300 W is used as the illumination light source, and infrared light emitted from the illumination light source is separately removed by the first reflecting filter 30a and the second reflecting filter 30b so that the first reflecting filter 30a satisfies Condition (1) defining the amount of transmission energy of infrared light of wavelengths more than 750 nm. If the first reflecting filter 30a fails to satisfy Condition (1), the amount of energy of infrared light transmitted through the first reflecting filter 30a will be increased, with a resulting heavy load of infrared light on the second reflecting filter 30b. As a result, the second reflecting filter 30b becomes more instrumental to improve the function by removing infrared light. For this purpose, the number of layers of the multilayered interference film evaporated on the transparent glass base plate must be increased. Consequently, the interference film has too many layers, thus extremely decreasing the strength of illumination light, and also becomes liable to undergo thermal influence. This causes the defect that the multilayered interference film is damaged by the load of infrared light. Hence, as in the sixth embodiment, it is desirable that even when the transmissive wavelength selecting filter unit is constructed with only the reflecting filters, the first reflecting filter 30a situated closer to the illumination light source satisfies Condition (1).

Although, in the sixth embodiment, ultraviolet light of wavelength less than 400 nm is cut off by the first reflecting filter 30a, it may also be removed by the second reflecting filter 30b.

Seventh embodiment

Figure 16:
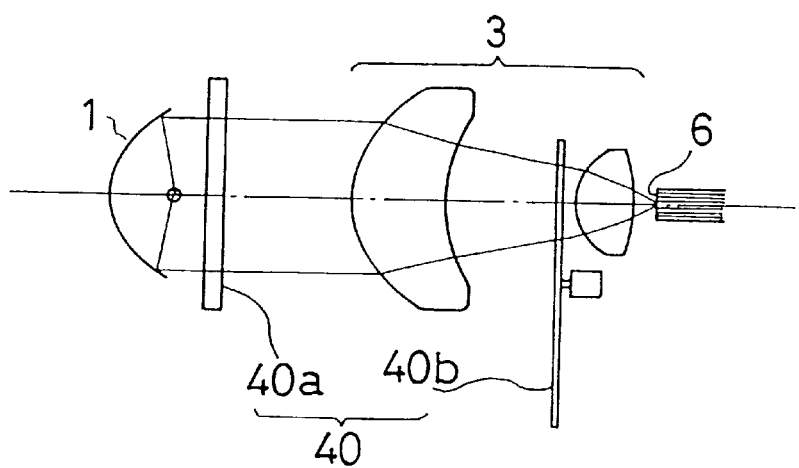
FIG. 16 is a view showing the optical arrangement of a seventh embodiment of the light source device for endoscopes according to the present invention.
Figure 17A:
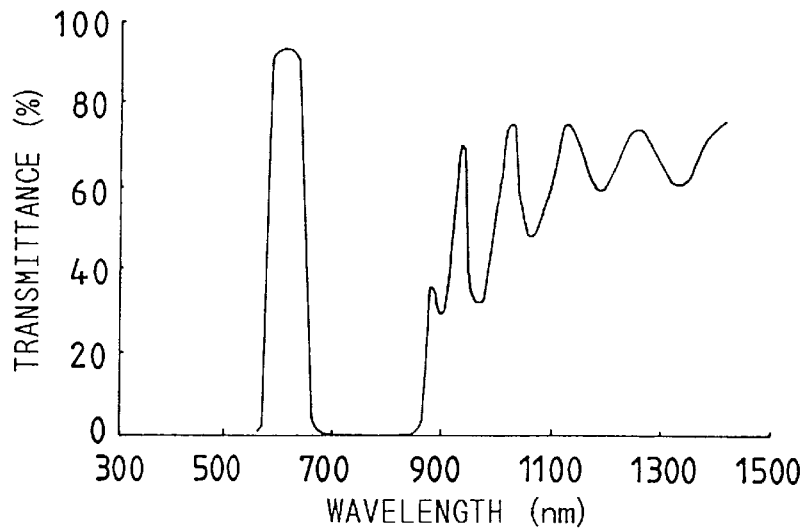
FIGS. 17A, 17B, and 17C are views showing transmittance characteristics of R, G, and B transmitting filters, respectively, in a rotary filter used in the seventh embodiment.
Figure 17B:
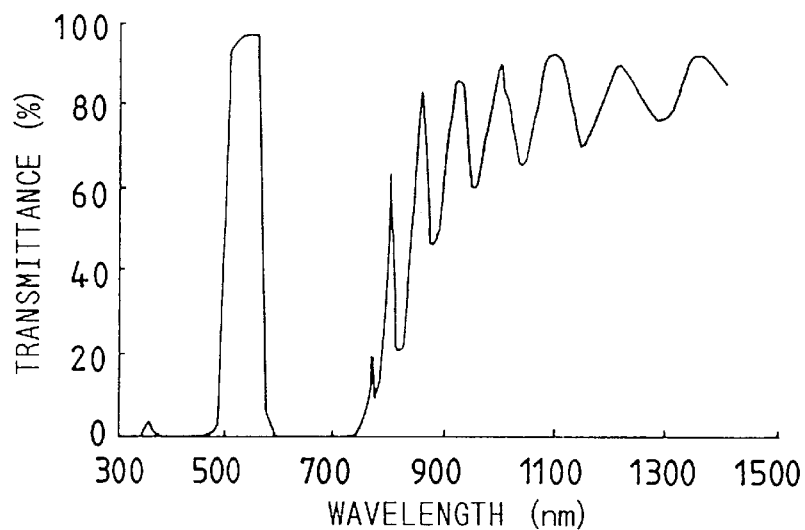
Figure 17C:
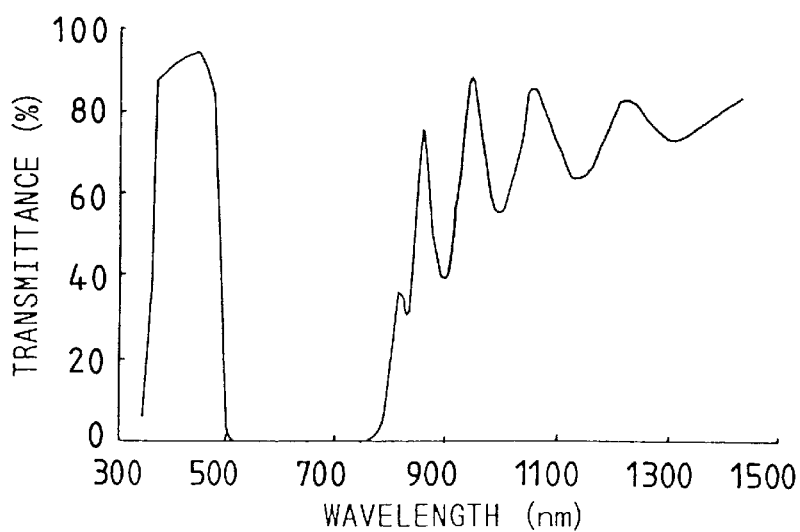

In this embodiment, as shown in FIG. 16, a transmissive wavelength selecting filter unit 40 includes, in order from the source side, a reflecting filter 40a given the property of reflecting light with unwanted wavelengths by a multilayered interference film coated by evaporation on a transparent glass base plate, and a rotary color filter 40b including color separating filters which are arranged in one disk along a concentric circle of the disk and are given properties of transmitting light in the wavelength bands of three colors of red, green, and blue by a multilayered interference film coated by evaporation on a transparent glass base plate to reflect light in the other wavelength bands. Since the reflecting filter 40a, as in the fifth and sixth embodiments, has the spectral transmittance characteristic shown in FIG. 6, light emitted from the illumination light source 1 is filtered such that light (ultraviolet) with wavelengths less than 400 nm and light (infrared) with wavelengths 750–1100 nm are removed by the reflecting filter 40a. Subsequently, light is time divided into three colors of red, green, and blue by the rotary color filter 40b composed of the color separating filers having the spectral transmittance characteristics shown in FIGS. 17A–17C. While the light of the three colors is concentrated at the entrance end of the light guide 6 in such a time-division mode, infrared light with wavelengths more than 1100 nm is scarcely removed and thus is always concentrated. Also, the condenser lens system 3 is placed between the reflecting filter 40a and the entrance end of the light guide 6.

The amount of energy of visible light at the entrance end of the light guide 6 is reduced to nearly ⅓ because the visible light is time divided into three colors. A temperature rise by the visible light at the entrance end of the light guide is thus much suppressed compared with the case where the light of three colors is incident thereon at the same time. It follows from this that even though some infrared light is incident to contribute to the temperature rise at the entrance end of the light guide 6, the entrance end of the light guide 6 will not be burned.

Furthermore, the reflecting filter 40a satisfies Condition (1), so that much of the infrared light emitted from the illumination source 1 is cut off by the reflecting filter 40a. Thus, even when remaining infrared light of wavelengths more than 1100 nm transmitted through the reflecting filter 40a, after being transmitted through the rotary color filter 40b, is concentrated at the entrance end of the light guide 6, the entrance end of the light guide 6 does not burn.

As in the seventh embodiment, even where the transmissive wavelength selecting filter unit is constructed with the combination of the reflecting filter and the rotary color filter, and infrared light is practically removed by only the reflecting filter, the amount of energy of infrared light transmitted through the reflecting filter is defined by Condition (1), and thereby the light source device in which the entrance end of the light guide does not burn can be realized. In this embodiment, a xenon lamp with a consumption power of 300 W is employed as the illumination light source.

What is claimed is:

1. A light source device for endoscopes, comprising:
   an illumination light source;
   a light guide;
   a condenser lens constructed and arranged to concentrate light that is emitted from said illumination light source at an entrance end of said light guide; and
   at least two transmissive wavelength selecting filters arranged between said illumination light source and the entrance end of said light guide,
   wherein a filter of said at least two transmissive selecting filters that is situated closer to said illumination light source transmits an amount of electromagnetic energy from said illumination light source that satisfies $$P \times \left\{ \int_\lambda R(\lambda)T(\lambda)d\lambda \bigg/ \int_\lambda R(\lambda)d\lambda \right\} < 60$$

where $R(\lambda)$ is a spectral energy emissivity of light with a wavelength $\lambda$ that is emitted from said illumination light source, $T(\lambda)$ is a spectral transmittance of the transmissive wavelength selecting filter disposed closer to said illumination light source for the wavelength $\lambda$, and P is a consumption power of a lamp used in said illumination light source, and where the integration with respect to the wavelength $\lambda$ is calculated over a wavelength range greater than or equal to 750 nm.

2. A light source device for endoscopes according to claim 1, wherein said at least two transmissive wavelength selecting filters, in combination, remove light having wavelengths up to 400 nm and remove light having wavelengths of at least 750 nm.

3. A light source device for endoscopes according to claim 2, wherein said transmissive wavelength selecting filters include a filter that has properties of transmitting light belonging to preselected first wavelength bands and of reflecting light in preselected second wavelength bands and a filter that has properties of transmitting light belonging to preselected third wavelength bands and of absorbing light in preselected fourth wavelength bands.

4. A light source device for endoscopes according to claim 2, wherein said transmissive wavelength selecting filters include filters each having properties of transmitting light belonging to preselected first wavelength bands and of reflecting light in preselected second wavelength bands.

5. A light source device for endoscopes according to claim 2, wherein, of said transmissive wavelength selecting filters, said filter disposed closer to said illumination light source has a property of blocking light having wavelengths in a range from 750 to 1100 nm.

* * * * *